United States Patent
Graf et al.

(10) Patent No.: US 6,946,531 B2
(45) Date of Patent: Sep. 20, 2005

(54) LOW MOLECULAR WEIGHT ETHYLENE INTERPOLYMERS AND POLYMERIZATION PROCESS

(75) Inventors: David D. Graf, Midland, MI (US); Jerzy Klosin, Midland, MI (US); Timothy A. Herzog, South Charleston, WV (US); Peter N. Nickias, Midland, MI (US); Carlos G. Ortiz, Houston, TX (US); Jorge Soto, Midland, MI (US); Ravi B. Shankar, Midland, MI (US); Daniel D. VanderLende, Sugar Land, TX (US)

(73) Assignee: Dow Global Technologies Inc., Midland, MI (US)

( * ) Notice: Subject to any disclaimer, the term of this patent is extended or adjusted under 35 U.S.C. 154(b) by 84 days.

(21) Appl. No.: 10/664,677

(22) Filed: Sep. 18, 2003

(65) Prior Publication Data

US 2004/0092680 A1 May 13, 2004

Related U.S. Application Data

(63) Continuation-in-part of application No. 10/123,277, filed on Apr. 15, 2002, now Pat. No. 6,825,147.
(60) Provisional application No. 60/290,696, filed on May 14, 2001, now abandoned.

(51) Int. Cl.$^7$ .............................. C08F 4/72; B01J 31/38
(52) U.S. Cl. ...................... 526/160; 526/161; 526/943; 502/117; 502/152; 502/155
(58) Field of Search ................................ 526/160, 161, 526/943; 502/117, 152, 155

(56) References Cited

U.S. PATENT DOCUMENTS

| | | | |
|---|---|---|---|
| 5,321,106 | A | 6/1994 | LaPointe |
| 5,374,696 | A | 12/1994 | Rosen et al. |
| 5,470,933 | A | 11/1995 | Mignani et al. |
| 5,486,632 | A | 1/1996 | Devore et al. |
| 5,541,349 | A | 7/1996 | Wilson et al. |
| 5,703,187 | A | 12/1997 | Timmers |
| 5,721,185 | A | 2/1998 | LaPointe et al. |
| 5,723,560 | A | 3/1998 | Canich |
| 5,866,704 | A | 2/1999 | Nickias et al. |
| 5,965,756 | A | 10/1999 | McAdon et al. |
| 6,054,544 | A | 4/2000 | Finlayson et al. |
| 6,825,147 | B2 * | 11/2004 | Klosin et al. ............... 502/117 |

FOREIGN PATENT DOCUMENTS

| | | |
|---|---|---|
| EP | 839834 | 6/2001 |
| WO | WO 97/15583 | 5/1997 |
| WO | WO 97/19463 | 5/1997 |
| WO | WO 98/10018 | 3/1998 |
| WO | WO 99/14221 | 3/1999 |
| WO | WO 02/074817 | 9/2002 |
| WO | WO 02/92610 | 11/2002 |

* cited by examiner

Primary Examiner—Robert D. Harlan

(57) ABSTRACT

Low molecular weight olefin polymers are prepared by a polymerization process employing titanium complexes comprising a 3-aryl-substituted cyclopentadienyl ring or substituted derivatives thereof as polymerization catalysts.

14 Claims, No Drawings

LOW MOLECULAR WEIGHT ETHYLENE INTERPOLYMERS AND POLYMERIZATION PROCESS

CROSS REFERENCE STATEMENT

This application is a continuation in part of application U.S. Ser. No. 10/123,277, filed Apr. 15, 2002, now U.S. Pat. No. 6,829,147 which claims the benefit of U.S. Provisional Application No. 60/290,696, filed May 14, 2001, now abandoned.

BACKGROUND OF THE INVENTION

This invention relates to Group 4 metal complexes containing an aryl substituted cyclopentadienyl ligand and to polymerization catalysts derived from such complexes that are particularly suitable for use in a polymerization process for preparing homopolymers and copolymers of olefins or diolefins, including copolymers comprising two or more olefins or diolefins such as copolymers comprising a monovinyl aromatic monomer and ethylene.

Constrained geometry metal complexes and methods for their preparation are disclosed in U.S. Pat. No. 5,703,187. This publication also teaches the preparation of certain novel copolymers of ethylene and a hindered vinyl monomer, including monovinyl aromatic monomers, having a pseudo-random incorporation of the hindered vinyl monomer therein. Additional teachings of constrained geometry catalysts may be found in U.S. Pat. Nos. 5,321,106, 5,721,185, 5,374,696, 5,470,993, 5,541,349, and 5,486,632, WO97/15583, WO97/19463.

In Table 1 of U.S. Pat. No. 5,723,560 and related patents, tetraphenylcyclopentadienyl-, 3,4-diphenylcyclopentadienyl-, and 2,5-diphenylcyclopentadienyl-ligands are listed. 2- and/or 3-substituted indenyl metal complexes are disclosed in U.S. Pat. No. 6,015,868. 3-Aryl-substituted indenyl metal complexes are disclosed in U.S. Pat. No. 5,866,704. Certain highly active, polyaromatic, metal complexes, especially derivatives of s-indacenyl- and cyclopentaphenanthrenyl-ligand groups are disclosed in U.S. Pat. No. 5,965,756 and U.S. Ser. No. 09/122,958, filed Jul. 27, 1998, (WO99/14221, published Mar. 25, 1999) respectively. Despite the advance in the art occasioned by the foregoing metal complexes, improved metal complexes that are capable of producing high styrene content ethylene/styrene interpolymers (ESI) and that are economical to prepare are continually desired. Accordingly, it would be desirable if there were provided metal complexes having acceptable catalytic properties that are also economical to produce.

SUMMARY OF THE INVENTION

According to the present invention there is provided 3-arylcyclopentadienyl-substituted metal complexes corresponding to the formula:

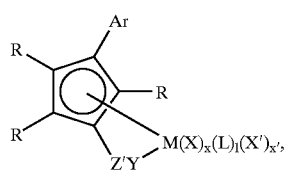

(I)

wherein,

Ar is an aryl group of from 6 to 30 atoms not counting hydrogen;

R independently each occurrence is hydrogen, Ar, or a group other than Ar selected from hydrocarbyl, trihydrocarbylsilyl, trihydrocarbylgermyl, halide, hydrocarbyloxy, trihydrocarbylsiloxy, bis(trihydrocarbylsilyl)amino, di(hydrocarbyl)amino, hydrocarbadiylamino, hydrocarbylimino, di(hydrocarbyl)phosphino, hydrocarbadiylphosphino, hydrocarbylsulfido, halo-substituted hydrocarbyl, hydrocarbyloxy-substituted hydrocarbyl, trihydrocarbylsilyl-substituted hydrocarbyl, trihydrocarbylsiloxy-substituted hydrocarbyl, bis(trihydrocarbylsilyl)amino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said R group having up to 40 atoms not counting hydrogen atoms;

M is titanium;

Z' is $SiR^6_2$, $CR^6_2$, $SiR^6_2SiR^6_2$, $CR^6_2CR^6_2$, $CR^6=CR^6$, $CR^6_2SiR^6_2$, $BR^6$, $BR^6L''$, or $GeR^6_2$;

Y is —O—, —S—, —$NR^5$—, —$PR^5$—; —$NR^5_2$, or —$PR^5_2$;

$R^5$, independently each occurrence, is hydrocarbyl, trihydrocarbylsilyl, or trihydrocarbylsilylhydrocarbyl, said $R^5$ having up to 20 atoms other than hydrogen, and optionally two $R^5$ groups or $R^5$ together with Y form a ring system;

$R^6$, independently each occurrence, is hydrogen, or a member selected from hydrocarbyl, hydrocarbyloxy, silyl, halogenated alkyl, halogenated aryl, —$NR^5_2$, and combinations thereof, said $R^6$ having up to 20 non-hydrogen atoms, and optionally, two $R^6$ groups form a ring system;

L'' is a monodentate or polydentate Lewis base optionally bonded to $R^6$;

X is hydrogen or a monovalent anionic ligand group having up to 60 atoms not counting hydrogen;

L independently each occurrence is a neutral ligating compound having up to 20 atoms, other than hydrogen, and optionally L and X are bonded together;

X' is a divalent anionic ligand group having up to 60 atoms other than hydrogen;

z is 0, 1 or 2;

x is 0, 1, 2, or 3;

l is a number from 0 to 2, and x' is 0 or 1.

The above compounds may exist as isolated crystals, as a mixture with other compounds, in the form of a solvated adduct, dissolved in a solvent, especially an organic liquid solvent, or in the form of a dimer.

Also, according to the present invention, there is provided a catalyst for polymerization of one or more addition polymerizable monomers comprising:

A. i) a metal complex of formula I, and
   ii) an activating cocatalyst,
   the molar ratio of i) to ii) being from 1:10,000 to 100:1, or B. the reaction product formed by converting a metal complex of formula I to an active catalyst by use of the foregoing activating cocatalyst or an activating technique.

Further according to the present invention there is provided a process for the polymerization of one or more addition polymerizable monomers comprising contacting one or more such monomers, especially one or more $C_{2-20}$ olefins, including cyclic olefins, under polymerization conditions with a catalyst comprising:

A. i) a metal complex of formula I, and
   ii) an activating cocatalyst,
   the molar ratio of i) to ii) being from 1:10,000 to 100:1, or B. the reaction product formed by converting a metal complex of formula I to an active catalyst by use of the foregoing activating cocatalyst or an activating technique.

Use of the present catalysts and processes is especially efficient in production of copolymers of two or more olefins, in particular, copolymers of ethylene and a vinylaromatic monomer, such as styrene, and interpolymers of three or more polymerizable monomers, including a vinylaromatic monomer over a wide range of polymerization conditions, and especially at elevated temperatures. They are especially useful for the formation of copolymers of ethylene and vinylaromatic monomers such as styrene (ES polymers), copolymers of ethylene, styrene, and a diene (ESDM polymers), and copolymers of ethylene, propylene and styrene (EPS polymers). Examples of suitable diene monomers include ethylidenenorbornene, 1,4-hexadiene or similar conjugated or nonconjugated dienes.

The catalysts of this invention may also be supported on a solid, particulated support material and used in the polymerization of addition polymerizable monomers, especially olefins, in a slurry or in a gas phase process. The catalyst may be prepolymerized with one or more olefin monomers in situ in a polymerization reactor or in a separate process with intermediate recovery of the prepolymerized catalyst prior to the primary polymerization process. Because the metal complexes do not contain fused aromatic rings, they are especially suited for use in the formation of polymer products having desirable biological response, taste, odor, and organoleptic properties, due to an absence of such polycyclic aromatic functionality.

DETAILED DESCRIPTION OF THE INVENTION

All reference to the Periodic Table of the Elements herein shall refer to the Periodic Table of the Elements, published and copyrighted by CRC Press, Inc., 1999. Also, any reference to a Group or Groups shall be to the Group or Groups as reflected in this Periodic Table of the Elements using the IUPAC system for numbering groups. For purposes of nomenclature herein, ring positions on the cyclopentadienyl ring are numbered beginning with the carbon attached to Z'. For purposes of United States patent practice, the contents of any patent, patent application or publication mentioned herein are hereby incorporated by reference in their entirety herein, especially with respect to the disclosure of organometallic structures, synthetic techniques and general knowledge in the art. As used herein the term "aromatic" or "aryl" refers to a polyatomic, cyclic, ring system containing $(4\delta+2)$ $\pi$-electrons, wherein $\delta$ is an integer greater than or equal to 1.

In the metal complexes, preferred L and L" groups are carbon monoxide; phosphines, especially trimethylphosphine, triethylphosphine, triphenylphosphine and bis(1,2-dimethylphosphino)ethane; $P(OR^4)_3$, wherein $R^4$ is $C_{1-20}$ hydrocarbyl; ethers, especially tetrahydrofuran; amines, especially pyridine, bipyridine, tetramethylethylenediamine (TMEDA), and triethylamine; olefins; and neutral conjugated dienes having from 4 to 40, preferably 5 to 40 carbon atoms. Complexes including neutral diene L groups and no X or X' groups are those wherein the metal is in the +2 formal oxidation state.

Further in reference to the metal complexes, X preferably is selected from the group consisting of hydro, halo, hydrocarbyl, silyl, and N,N-dialkylamino-substituted hydrocarbyl. The number of X groups depends on the oxidation state of M, whether Y is divalent or not and whether any neutral diene groups or divalent X' groups are present. The skilled artisan will appreciate that the quantity of the various substituents and the identity of Z'Y are chosen to provide charge balance, thereby resulting in a neutral metal complex.

For example, when Z'Y is divalent, and x is zero, x' is two less than the formal oxidation state of M. When Z'Y contains one neutral two electron coordinate-covalent bonding site, and M is in a formal oxidation state of +3, x may equal zero and x' equal 1, or x may equal 2 and x' equal zero. In a final example, if M is in a formal oxidation state of +2, Z'Y may be a divalent ligand group, whereupon x and x' are both equal to zero and one neutral L ligand group may be present.

Suitable Ar groups for use herein include aromatic hydrocarbyl groups, or aromatic groups containing nitrogen, oxygen, boron, silicon, phosphorus and/or sulfur in a ring thereof in addition to carbon, as well as $di(C_{1-10}$ hydrocarbyl)amino-, $(C_{1-20}$hydrocarbadiyl)amino-, $C_{1-10}$ hydrocarbyloxy-, and $tri(C_{1-10}$ hydrocarbyl)silane- substituted derivatives thereof. Examples include phenyl, tolyl (all isomers), ethylphenyl (all isomers), trimethylphenyl (all isomers), methoxyphenyl (all isomers), N,N-dimethylaminophenyl (all isomers), trimethylsilylphenyl (all isomers), naphthyl, 4-bisphenyl, pyrrol-1-yl, and 1-methylpyrrol-3-yl.

Preferred compounds of the invention correspond to the formula I wherein independently each occurrence:

Ar is phenyl, naphthyl, 4-bisphenyl, 3-(N,N-dimethylamino)phenyl, 4-methoxyphenyl, 4-methylphenyl, pyrrol-1-yl, or 1-methylpyrrol-3-yl;

R is hydrogen, methyl or Ar;

X is chloride, methyl or benzyl;

X' is 2,3-dimethyl-1,3-butenediyl;

L is 1,3-pentadiene or 1,4-diphenyl-1,3-butadiene;

Y is $-NR^5-$;

Z' is $SiR^6_2$;

$R^5$ each occurrence is independently hydrocarbyl;

$R^6$ each occurrence is independently methyl;

x is 0 or 2;

l is 0 or 1; and x' is 0 or 1;

with the proviso that:

when x is 2, x' is zero, and M is in the +4 formal oxidation state, when x is 0 and x' is 1, M is in the +4 formal oxidation state, and when x and x' are both 0, l is 1, and M is in the +2 formal oxidation state.

More preferably, R in at least one additional occurrence, is selected from the group consisting of Ar. Highly preferably, at least one of the foregoing additional Ar groups is attached to the 4-position of the cyclopentadienyl ring. Most highly preferably the metal complexes are substituted at both the 3- and 4-positions with an Ar group.

Examples of suitable metal complexes according to the present invention are:

(3-phenylcyclopentadien-1-yl)dimethyl(t-butylamido) silanetitanium dichloride, (3-phenylcyclopentadien-1-yl)dimethyl(t-butylamido) silanetitanium dimethyl, (3-phenylcyclopentadien-1-yl)dimethyl(t-butylamido) silanetitanium (II) 1,4-diphenyl-1,3-butadiene;

(3-(pyrrol-1-yl)cyclopentadien-1-yl)dimethyl(t-butylamido) silanetitanium dichloride, (3-(pyrrol-1-yl)cyclopentadien-1-yl)dimethyl(t-butylamido) silanetitanium dimethyl, (3-(pyrrol-1-yl)cyclopentadien-1-yl))dimethyl(t-butylamido)silanetitanium (II) 1,4-diphenyl-1,3-butadiene;

(3-(1-methylpyrrol-3-yl)cyclopentadien-1-yl)dimethyl(t-butylamido)silanetitanium dichloride,
(3-(1-methylpyrrol-3-yl)cyclopentadien-1-yl)dimethyl(t-butylamido)silanetitanium dimethyl,
(3-(1-methylpyrrol-3-yl)cyclopentadien-1-yl)dimethyl(t-butylamido)silanetitanium (II) 1,4-diphenyl-1,3-butadiene;
(3,4-diphenylcyclopentadien-1-yl)dimethyl(t-butylamido)silanetitanium dichloride,
(3,4-diphenylcyclopentadien-1-yl)dimethyl(t-butylamido)silanetitanium dimethyl,
(3,4-diphenylcyclopentadien-1-yl)dimethyl(t-butylamido)silanetitanium (II) 1,3-pentadiene;
(3-(3-N,N-dimethylamino)phenyl)cyclopentadien-1-yl)dimethyl(t-butylamido)silanetitanium dichloride,
(3-(3-N,N-dimethylamino)phenylcyclopentadien-1-yl)dimethyl(t-butylamido)silanetitanium dimethyl,
(3-(3-N,N-dimethylamino)phenylcyclopentadien-1-yl)dimethyl(t-butylamido)silanetitanium (II) 1,4-diphenyl-1,3-butadiene;
(3-(4-methoxyphenyl)-4-methylcyclopentadien-1-yl)dimethyl(t-butylamido)silanetitanium dichloride,
(3-(4-methoxyphenyl)-4-phenylcyclopentadien-1-yl)dimethyl(t-butylamido)silanetitanium dimethyl,
(3-4-methoxyphenyl)-4-phenylcyclopentadien-1-yl)dimethyl(t-butylamido)silanetitanium(II) 1,4-diphenyl-1,3-butadiene;
(3-phenyl-4-methoxycyclopentadien-1-yl)dimethyl(t-butylamido)silanetitanium dichloride,
(3-phenyl-4-methoxycyclopentadien-1-yl)dimethyl(t-butylamido)silanetitanium dimethyl,
(3-phenyl-4-methoxycyclopentadien-1-yl)dimethyl(t-butylamido)silanetitanium (II) 1,4-diphenyl-1,3-butadiene;
(3-phenyl-4-(N,N-dimethylamino)cyclopentadien-1-yl)dimethyl(t-butylamido)silanetitanium dichloride,
(3-phenyl-4-(N,N-dimethylamino)cyclopentadien-1-yl)dimethyl(t-butylamido)silanetitanium dimethyl,
(3-phenyl-4-(N,N-dimethylamnino)cyclopentadien-1-yl)dimethyl(t-butylamido)silanetitanium(II) 1,4-diphenyl-1,3-butadiene;
2-methyl-(3,4-di(4-methylphenyl)cyclopentadien-1-yl)dimethyl(t-butylamido)silanetitanium dichloride,
2-methyl-(3,4-di(4-methylphenyl)cyclopentadien-1-yl)dimethyl(t-butylamido)silanetitanium dimethyl,
2-methyl-(3,4-di(4-methylphenyl)cyclopentadien-1-yl)dimethyl(t-butylamido)silanetitanium(II) 1,4-diphenyl-1,3-butadiene;
((2,3-diphenyl)-4-(N,N-dimethylamino)cyclopentadien-1-yl)dimethyl(t-butylamido)silane titanium dichloride,
((2,3-diphenyl)-4-(N,N-dimethylamino)cyclopentadien-1-yl)dimethyl(t-butylamido)silane titanium dimethyl,
((2,3-diphenyl)-4-(N,N-dimethylamino)cyclopentadien-1-yl)dimethyl(t-butylarmido)silanetitanium (II) 1,4-diphenyl-1,3-butadiene;
(2,3,4-triphenyl-5-methylcyclopentadien-1-yl)dimethyl(t-butylamido)silanetitanium dichloride,
(2,3,4-triphenyl-5-methylcyclopentadien-1-yl)dimethyl(t-butylamido)silanetitanium dimethyl,
(2,3,4-triphenyl-5-methylcyclopentadien-1-yl)dimethyl(t-butylamido)silanetitanium (II) 1,4-diphenyl-1,3-butadiene;
(3-phenyl-4-methoxycyclopentadien-1-yl)dimethyl(t-butylamido)silanetitanium dichloride,
(3-phenyl-4-methoxycyclopentadien-1-yl)dimethyl(t-butylamido)silanetitanium dimethyl,
(3-phenyl-4-methoxycyclopentadien-1-yl)dimethyl(t-butylamido)silanetitanium (II) 1,4-diphenyl-1,3-butadiene;
(2,3-diphenyl-4-(n-butyl)cyclopentadien-1-yl)dimethyl(t-butylamido)silanetitanium dichloride,
(2,3-diphenyl-4-(n-butyl)cyclopentadien-1-yl)dimethyl(t-butylamido)silanetitanium dimethyl,
(2,3-diphenyl-4-(n-butyl)cyclopentadien-1-yl)dimethyl(t-butylamido)silanetitanium (II) 1,4-diphenyl-1,3-butadiene;
(2,3,4,5-tetraphenylcyclopentadien-1-yl)dimethyl(t-butylamido)silanetitanium dichloride,
(2,3,4,5-tetraphenylcyclopentadien-1-yl)dimethyl(t-butylamido)silanetitanium dimethyl, and
(2,3,4,5-tetraphenylcyclopentadien-1-yl)dimethyl(t-butylamido)silanetitanium (II) 1,4-diphenyl-1,3-butadiene.

The complexes are rendered catalytically active by combination with an activating cocatalyst or use of an activating technique, such as those that are previously known in the art for use with Group 4 metal olefin polymerization complexes. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl) borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium salts of compatible, noncoordinating anions; bulk electrolysis (explained in more detail hereinafter); and combinations of the foregoing activating cocatalysts and techniques. A preferred ion forming compound is a tri($C_{1-20}$-hydrocarbyl)ammonium salt of a tetrakis (fluoroaryl)borate, especially a tetrakis(pentafluorophenyl) borate. The foregoing activating cocatalysts and activating techniques have been previously taught with respect to different metal complexes in the following references: EP-A-277,003, U.S. Pat. Nos. 5,153,157, 5,064,802, 5,321,106, 5,721,185, 5,350,723, 5,425,872, 5,625,087, 5,883,204, 5,919,983, 5,783,512, WO 99/15534, and U.S. Ser. No. 09/251,664, filed Feb. 17, 1999 (WO99/42467).

Combinations of neutral Lewis acids, especially the combination of a trialkylaluminum compound having from 1 to 4 carbons in each alkyl group and a halogenated tri(hydrocarbyl)boron compound having from 1 to 20 carbons in each hydrocarbyl group, especially tris(pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. Preferred molar ratios of Group 4 metal complex: tris(pentafluorophenyl)borane: alumoxane are from 1:1:1 to 1:10:30, more preferably from 1:1:1.5 to 1:5:10.

Suitable ion forming compounds useful as cocatalysts in one embodiment of the present invention comprise a cation which is a Brønsted acid capable of donating a proton, and a compatible, noncoordinating anion, $A^-$. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gallium, niobium or tantalum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

$$(L^*\text{-}H)_d^+(A)^{d-}$$

wherein:

L* is a neutral Lewis base;

(L*-H)+ is a conjugate Brønsted acid of L*;

$A^{d-}$ is a noncoordinating, compatible anion having a charge of d−, and d is an integer from 1 to 3.

More preferably $A^{d-}$ corresponds to the formula:

$$[M'Q_4]^-;$$

wherein:

M' is boron or aluminum in the +3 formal oxidation state; and

Q independently each occurrence is selected from hydride, dialkylamido, halide, hydrocarbyl, hydrocarbyloxide, halo-substituted hydrocarbyl, halo-substituted hydrocarbyloxy, and halo-substituted silylhydrocarbyl radicals (including perhalogenated hydrocarbyl-perhalogenated hydrocarbyloxy- and perhalogenated silylhydrocarbyl radicals), said Q having up to 20 carbons with the proviso that in not more than one occurrence is Q halide. Examples of suitable hydrocarbyloxide Q groups are disclosed in U.S. Pat. 5,296,433.

In a more preferred embodiment, d is one, that is, the counter ion has a single negative charge and is A−. Activating cocatalysts comprising boron which are particularly useful in the preparation of catalysts of this invention may be represented by the following general formula:

$$(L^*\text{-}H)^+(BQ_4)^-;$$

wherein:

L* is as previously defined;

B is boron in a formal oxidation state of 3; and

Q is a hydrocarbyl-, hydrocarbyloxy-, fluorohydrocarbyl-, fluorohydrocarbyloxy-, hydroxyfluorohydrocarbyl-, dihydrocarbylaluminumoxyfluorohydrocarbyl-, or fluorinated silylhydrocarbyl-group of up to 20 nonhydrogen atoms, with the proviso that in not more than one occasion is Q hydrocarbyl. Most preferably, Q is each occurrence a fluorinated aryl group, especially, a pentafluorophenyl group.

Preferred Lewis base salts are ammonium salts, more preferably trialkyl-ammonium- or dialkylarylammonium-salts containing one or more $C_{12-40}$ alkyl groups. The latter cocatalysts have been found to be particularly suitable for use in combination with not only the present metal complexes but other Group 4 metallocenes as well.

Illustrative, but not limiting, examples of boron compounds which may be used as an activating cocatalyst in the preparation of the improved catalysts of this invention (as well as previously known Group 4 metal catalysts) are tri-substituted ammonium salts such as:

trimethylammonium tetrakis(pentafluorophenyl) borate,
triethylammonium tetrakis(pentafluorophenyl) borate,
tripropylammonium tetrakis(pentafluorophenyl) borate,
tri(n-butyl)ammonium tetrakis(pentafluorophenyl) borate,
tri(sec-butyl)ammonium tetrakis(pentafluorophenyl) borate,
N,N-dimethylanilinium tetrakis(pentafluorophenyl) borate,
N,N-dimethylanilinium n-butyltris(pentafluorophenyl) borate,
N,N-dimethylanilinium benzyltris(pentafluorophenyl) borate,
N,N-dimethylanilinium tetrakis(4-(t-butyldimethylsilyl)-2,3,5,6-tetrafluorophenyl) borate,
N,N-dimethylanilinium tetrakis(4-(triisopropylsilyl)-2,3,5,6-tetrafluorophenyl) borate,
N,N-dimethylanilinium pentafluorophenoxytris(pentafluorophenyl) borate,
N,N-diethylanilinium tetrakis(pentafluorophenyl) borate,
N,N-dimethyl-2,4,6-trimethylanilinium tetrakis(pentafluorophenyl) borate,
dimethyltetradecylammonium tetrakis(pentafluorophenyl) borate,
dimethylhexadecylammonium tetrakis(pentafluorophenyl) borate,
dimethyloctadecylammonium tetrakis(pentafluorophenyl) borate,
methylditetradecylammonium tetrakis(pentafluorophenyl) borate,
methylditetradecylammonium (hydroxyphenyl)tris(pentafluorophenyl) borate,
methylditetradecylammonium (diethylaluminoxyphenyl)tris(pentafluorophenyl) borate,
methyldihexadecylammonium tetrakis(pentafluorophenyl) borate,
methyldihexadecylammonium (hydroxyphenyl)tris(pentafluorophenyl) borate,
methyldihexadecylammonium (diethylaluminoxyphenyl)tris(pentafluorophenyl) borate,
methyldioctadecylammonium tetrakis(pentafluorophenyl) borate,
methyldioctadecylammonium (hydroxyphenyl)tris(pentafluorophenyl) borate,
methyldioctadecylammonium (diethylaluminoxyphenyl)tris(pentafluorophenyl) borate,
methyldioctadecylammonium tetrakis(pentafluorophenyl) borate,
phenyldioctadecylammonium tetrakis(pentafluorophenyl) borate,
phenyldioctadecylammonium (hydroxyphenyl)tris(pentafluorophenyl) borate,
phenyldioctadecylammonium (diethylaluminoxyphenyl)tris(pentafluorophenyl) borate, (2,4,6-trimethylphenyl)dioctadecylammonium tetrakis (pentafluorophenyl) borate,
(2,4,6-trimethylphenyl)dioctadecylammonium (hydroxyphenyl)tris(pentafluorophenyl)-borate,
(2,4,6-trimethylphenyl)dioctadecylammonium (diethylaluminoxyphenyl) tris(pentafluorophenyl)borate,
(2,4,6-trifluorophenyl)dioctadecylammnonium tetrakis (pentafluorophenyl)borate,
(2,4,6-trifluorophenyl)dioctadecylammonium (hydroxyphenyl)tris(pentafluorophenyl)-borate,
(2,4,6-trifluorophenyl)dioctadecylammonium (diethylaluminoxyphenyl)tris(pentafluoro-phenyl) borate,
(pentafluorophenyl)dioctadecylammonium tetrakis (pentafluorophenyl)borate,
(pentafluorophenyl)dioctadecylammonium (hydroxyphenyl)tris(pentafluorophenyl)-borate,
(pentafluorophenyl)dioctadecylammonium (diethylaluminoxyphenyl)tris(pentafluoro-phenyl) borate,
(p-trifluoromethylphenyl)dioctadecylammonium tetrakis (pentafluorophenyl)borate,
(p-trifluoromethylphenyl)dioctadecylammonium (hydroxyphenyl)tris(pentafluoro-phenyl) borate,
(p-trifluoromethylphenyl)dioctadecylammonium (diethylaluminoxyphenyl)tris(penta-fluorophenyl) borate,
p-nitrophenyldioctadecylammonium tetrakis (pentafluorophenyl)borate,
p-nitrophenyldioctadecylammonium (hydroxyphenyl)tris (pentafluorophenyl) borate,
p-nitrophenyldioctadecylammonium (diethylaluminoxyphenyl)tris(pentafluorophenyl) borate,
and mixtures of the foregoing,
dialkyl ammonium salts such as:
di-(i-propyl)ammonium tetrakis(pentafluorophenyl) borate,
methyloctadecylammonium tetrakis(pentafluorophenyl) borate,
methyloctadodecylammonium tetrakis(pentafluorophenyl) borate, and
dioctadecylammonium tetrakis(pentafluorophenyl) borate;
tri-substituted phosphonium salts such as:
triphenylphosphonium tetrakis(pentafluorophenyl) borate,
methyldioctadecylphosphonium tetrakis(pentafluorophenyl) borate, and
tri(2,6-dimethylphenyl)phosphonium tetrakis (pentafluorophenyl) borate;
di-substituted oxonium salts such as:
diphenyloxonium tetrakis(pentafluorophenyl) borate,
di(o-tolyl)oxonium tetrakis(pentafluorophenyl) borate, and
di(octadecyl)oxonium tetrakis(pentafluorophenyl) borate;
di-substituted sulfonium salts such as:
di(o-tolyl)sulfonium tetrakis(pentafluorophenyl) borate, and
methylcotadecylsulfonium tetrakis(pentafluorophenyl) borate.

Preferred trialkylarnmonium cations are methyldioctadecylammonium and dimethyloctadecylammonium. The use of the above Brønsted acid salts as activating cocatalysts for addition polymerization catalysts is known in the art, having been disclosed in U.S. Pat. Nos. 5,064,802, 5,919,983, 5,783,512 and elsewhere. Preferred dialkylarylammonium cations are fluorophenyldioctadecylammonium-, perfluorophenyldioctacecylammonium- and p-trifluoromethylphenyldi(octadecyl)ammonium cations. It should be noted that certain of the cocatalysts, especially those containing a hydroxyphenyl ligand in the borate anion, may require the addition of a Lewis acid, especially a trialkylaluminum compound, to the polymerization mixture or the catalyst composition, in order to form the active catalyst composition.

Another suitable ion forming, activating cocatalyst comprises a salt of a cationic oxidizing agent and a noncoordinating, compatible anion represented by the formula:

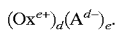

$(Ox^{e+})_d(A^{d-})_e$.

wherein:
$Ox^{e+}$ is a cationic oxidizing agent having a charge of e+;
e is an integer from 1 to 3; and
$A^{d-}$ and d are as previously defined.

Examples of cationic oxidizing agents include: ferrocenium, hydrocarbyl-substituted ferrocenium, $Ag^{+'}$ or $Pb^{+2}$. Preferred embodiments of $A^{d-}$ are those anions previously defined with respect to the Brønsted acid containing activating cocatalysts, especially tetrakis (pentafluorophenyl)borate. The use of the above salts as activating cocatalysts for addition polymerization catalysts is known in the art, having been disclosed in U.S. Pat. No. 5,321,106.

Another suitable ion forming, activating cocatalyst comprises a compound which is a salt of a carbenium ion and a noncoordinating, compatible anion represented by the formula:

$ⓒ^+A^-$ wherein:
$ⓒ^+$ is a $C_{1-20}$ carbenium ion; and
$A^-$ is as previously defined. A preferred carbenium ion is the trityl cation, that is triphenylmethylium. The use of the above carbenium salts as activating cocatalysts for addition polymerization catalysts is known in the art, having been disclosed in U.S. Pat. No. 5,350,723.

A further suitable ion forming, activating cocatalyst comprises a compound which is a salt of a silylium ion and a noncoordinating, compatible anion represented by the formula:

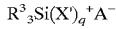

$R^3_3Si(X')_q{}^+A^-$ wherein:
$R^3$ is $C_{1-10}$ hydrocarbyl, and X', q and $A^-$ are as previously defined.

Preferred silylium salt activating cocatalysts are trimethylsilylium tetrakispentafluorophenylborate, triethylsilylium tetrakispentafluorophenylborate and ether substituted adducts thereof. The use of the above silylium salts as activating cocatalysts for addition polymerization catalysts is known in the art, having been disclosed in U.S. Pat. No. 5,625,087.

Certain complexes of alcohols, mercaptans, silanols, and oximes with tris(pentafluorophenyl)borane are also effective catalyst activators and may be used according to the present invention. Such cocatalysts are disclosed in U.S. Pat. No. 5,296,433.

Another class of suitable catalyst activators are expanded anionic compounds corresponding to the formula:

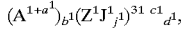

$(A^{1+a^1})_{b^1}(Z^1J^1{}_j)^{31\ c^1}{}_{d^1}$, wherein:
$A^1$ is a cation of charge $+a^1$,
$Z^1$ is an anion group of from 1 to 50, preferably 1 to 30 atoms, not counting hydrogen atoms, further containing two or more Lewis base sites;
$J^1$ independently each occurrence is a Lewis acid coordinated to at least one Lewis base site of $Z^1$, and optionally two or more such $J^1$ groups may be joined together in a moiety having multiple Lewis acidic functionality, $j^1$ is a number from 2 to 12 and $a^1$, $b^1$, $c^1$, and $d^1$ are integers from 1 to 3, with the proviso that $a^1 \times b^1$ is equal to $c^1 \times d^1$.

The foregoing cocatalysts (illustrated by those having imidazolide, substituted imidazolide, imidazolinide, substituted imidazolinide, benzimidazolide, or substituted benzimidazolide anions) may be depicted schematically as follows:

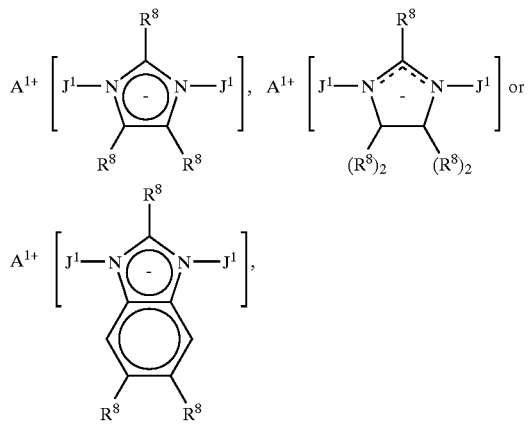

wherein:

$A^{1+}$ is a monovalent cation as previously defined, and preferably is a trihydrocarbyl ammonium cation, most preferably containing one or two $C_{10-40}$ alkyl groups, especially the methylbis(tetradecyl)ammonium- or methylbis(octadecyl)ammonium-cation, $R^8$, independently each occurrence, is hydrogen or a halo, hydrocarbyl, halocarbyl, halohydrocarbyl, silylhydrocarbyl, or silyl, (including mono-, di- and tri(hydrocarbyl)silyl) group of up to 30 atoms not counting hydrogen, preferably $C_{1-20}$ alkyl, and $J^1$ is tris(pentafluorophenyl)borane or tris(pentafluorophenyl)aluminane.

Examples of these catalyst activators include the trihydrocarbylammonium-, especially, methylbis(tetradecyl)ammonium- or methylbis(octadecyl)ammonium-salts of:
bis(tris(pentafluorophenyl)borane)imidazolide,
bis(tris(pentafluorophenyl)borane)-2-undecylimidazolide,
  bis(tris(pentafluorophenyl)borane)-2-heptadecylimidazolide, bis(tris(pentafluorophenyl)borane)-4,5-bis(undecyl)imidazolide,
bis(tris(pentafluorophenyl)borane)-4,5-bis(heptadecyl)imidazolide,
bis(tris(pentafluorophenyl)borane)imidazolinide,
bis(tris(pentafluorophenyl)borane)-2-undecylimidazolinide,
  bis(tris(pentafluorophenyl)borane)-2-heptadecylimidazolinide, bis(tris(pentafluorophenyl)borane)-4,5-bis(undecyl)imidazolinide,
bis(tris(pentafluorophenyl)borane)-4,5-bis(heptadecyl)imidazolinide,
bis(tris(pentafluorophenyl)borane)-5,6-dimethylbenzimidazolide,
bis(tris(pentafluorophenyl)borane)-5,6-bis(undecyl)benzimidazolide,
bis(tris(pentafluorophenyl)alumane)imidazolide,
bis(tris(pentafluorophenyl)alumane)-2-undecylimidazolide,
  bis(tris(pentafluorophenyl)alumane)-2-heptadecylimidazolide, bis(tris(pentafluorophenyl)alumane)-4,5-bis(undecyl)imidazolide,
bis(tris(pentafluorophenyl)alumane)-4,5-bis(heptadecyl)imidazolide,
bis(tris(pentafluorophenyl)alumane)imidazolinide,
bis(tris(pentafluorophenyl)alumane)-2-undecylimidazolinide,
  bis(tris(pentafluorophenyl)alumane)-2-heptadecylimidazolinide, bis(tris(pentafluorophenyl)alumane)-4,5-bis(undecyl)imidazolinide,
bis(tris(pentafluorophenyl)alumane)-4,5-bis(heptadecyl)imidazolinide,
bis(tris(pentafluorophenyl)alumane)-5,6-dimethylbenzimidazolide, and
bis(tris(pentafluorophenyl)alumane)-5,6-bis(undecyl)benzimidazolide.

A further class of suitable activating cocatalysts include cationic Group 13 salts corresponding to the formula:

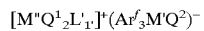

[M"$Q^1_2$L'$_{1'}$]$^+$(Ar$^f_3$M'Q$^2$)$^-$ wherein:

M" is aluminum, gallium, or indium;

M' is boron or aluminum;

$Q^1$ is $C_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more $Q^1$ groups may be covalently linked with each other to form one or more fused rings or ring systems;

$Q^2$ is an alkyl group, optionally substituted with one or more cycloalkyl or aryl groups, said $Q^2$ having from 1 to 30 carbons;

L' is a monodentate or polydentate Lewis base, preferably L' is reversibly coordinated to the metal complex such that it may be displaced by an olefin monomer, more preferably L' is a monodentate Lewis base;

1' is a number greater than zero indicating the number of Lewis base moieties, L', and Ar$^f$ independently each occurrence is an anionic ligand group; preferably Ar$^f$ is selected from the group consisting of halide, $C_{1-20}$ halohydrocarbyl, and $Q^1$ ligand groups, more preferably Ar$^f$ is a fluorinated hydrocarbyl moiety of from 1 to 30 carbon atoms, most preferably Ar$^f$ is a fluorinated aromatic hydrocarbyl moiety of from 6 to 30 carbon atoms, and most highly preferably Ar$^f$ is a perfluorinated aromatic hydrocarbyl moiety of from 6 to 30 carbon atoms.

Examples of the foregoing Group 13 metal salts are alumicinium tris(fluoroaryl)borates or gallicinium tris(fluoroaryl)borates corresponding to the formula:

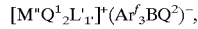

[M"$Q^1_2$L'$_{1'}$]$^+$(Ar$^f_3$BQ$^2$)$^-$, wherein M" is aluminum or gallium; $Q^1$ is $C_{1-20}$ hydrocarbyl, preferably $C_{1-8}$ alkyl; Ar$^f$ is perfluoroaryl, preferably pentafluorophenyl; and $Q^2$ is $C_{1-8}$ alkyl, preferably $C_{1-8}$ alkyl. More preferably, $Q^1$ and $Q^2$ are identical $C_{1-8}$ alkyl groups, most preferably, methyl, ethyl or octyl.

The foregoing activating cocatalysts may also be used in combination. An especially preferred combination is a mixture of a tri(hydrocarbyl)aluminum or tri(hydrocarbyl)borane compound having from 1 to 4 carbons in each hydrocarbyl group or an ammonium borate with an oligomeric or polymeric alumoxane compound.

The molar ratio of catalyst/cocatalyst employed preferably ranges from 1:10,000 to 100:1, more preferably from 1:5000 to 10:1, most preferably from 1:1000 to 1:1.

Alumoxane, when used by itself as an activating cocatalyst, is employed in large quantity, generally at least 100 times the quantity of metal complex on a molar basis. Tris (pentafluorophenyl)borane, where used as an activating cocatalyst is employed in a molar ratio to the metal complex of form 0.5:1 to 10:1, more preferably from 1:1 to 6:1 most preferably from 1:1 to 5:1. The remaining activating cocatalysts are generally employed in approximately equimolar quantity with the metal complex.

The catalysts, whether or not supported in any suitable manner, may be used to polymerize ethylenically unsaturated monomers having from 2 to 100,000 carbon atoms either alone or in combination. Preferred addition polymerizable monomers for use herein include olefins, diolefins and mixtures thereof. Preferred olefins are aliphatic or aromatic compounds containing vinylic unsaturation as well as cyclic compounds containing ethylenic unsaturation. Examples of the latter include cyclobutene, cyclopentene, norbornene, and norbornene derivatives that are substituted in the 5- and 6-positions with $C_{1-20}$ hydrocarbyl groups. Preferred diolefins are $C_{4-40}$ diolefin compounds, including ethylidene norbornene, 1,4-hexadiene, norbornadiene, and the like. The catalysts and processes herein are especially suited for use in preparation of ethylene/1-butene, ethylene/1-hexene, ethylene/styrene, ethylene/propylene, ethylene/1-pentene, ethylene/4-methyl-1-pentene and ethylene/1-octene copolymers as well as terpolymers of ethylene, propylene and a nonconjugated diene, such as, for example, EPDM terpolymers.

Most preferred monomers include the $C_{2-20}$ α-olefins, especially ethylene, propylene, isobutylene, 1-butene, 1-pentene, 1-hexene, 3-methyl-1-pentene, 4-methyl-1-pentene, 1-octene, 1-decene, long chain macromolecular α-olefins, and mixtures thereof. Other preferred monomers include styrene, $C_{1-4}$ alkyl substituted styrene, ethylidenenorbornene, 1,4-hexadiene, 1,7-octadiene, vinylcyclohexane, 4-vinylcyclohexene, divinylbenzene, and mixtures thereof with ethylene. Long chain macromolecular α-olefins are vinyl terminated polymeric remnants formed in situ during continuous solution polymerization reactions. Under suitable processing conditions such long chain macromolecular units are readily polymerized into the polymer product along with ethylene and other short chain olefin monomers to give small quantities of long chain branching in the resulting polymer.

Preferred monomers include a combination of ethylene and one or more comonomers selected from monovinyl aromatic monomers, 4-vinylcyclohexene, vinylcyclohexane, norbornadiene, ethylidene-norbornene, $C_{3-10}$ aliphatic α-olefins (especially propylene, isobutylene, 1-butene, 1-hexene, 3-methyl-1-pentene, 4-methyl-1-pentene, and 1-octene), and $C_{4-40}$ dienes. Most preferred monomers are mixtures of ethylene and styrene; mixtures of ethylene, propylene and styrene; mixtures of ethylene, styrene and a nonconjugated diene, especially ethylidenenorbornene or 1,4-hexadiene, and mixtures of ethylene, propylene and a nonconjugated diene, especially ethylidenenorbornene or 1,4-hexadiene.

In general, the polymerization may be accomplished at conditions well known in the prior art for Ziegler-Natta or Kaminsky-Sinn type polymerization reactions, that is, temperatures from 0–250° C., preferably 30 to 200° C. and pressures from atmospheric to 10,000 atmospheres. Suspension, solution, slurry, gas phase, solid state powder polymerization or other process condition may be employed if desired. A support, especially silica, alumina, or a polymer (especially poly(tetrafluoroethylene) or a polyolefin) may be employed, and desirably is employed when the catalysts are used in a gas phase polymerization process. The support is preferably employed in an amount to provide a weight ratio of catalyst (based on metal):support from $1:10^6$ to $1:10^3$, more preferably from $1:10^6$ to $1:10^4$.

In most polymerization reactions the molar ratio of catalyst:polymerizable compounds employed is from $10^{-12}:1$ to $10^{-1}:1$, more preferably from $10^{-9}:1$ to $10^{-5}:1$.

Suitable solvents use for solution polymerization are liquids that are substantially inert under process conditions encountered in their usage. Examples include straight and branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and alkyl-substituted aromatic compounds such as benzene, toluene, xylene, and ethylbenzene. Suitable solvents also include liquid olefins which may act as monomers or comonomers.

The catalysts may be utilized in combination with at least one additional homogeneous or heterogeneous polymerization catalyst in the same reactor or in separate reactors connected in series or in parallel to prepare polymer blends having desirable properties. An example of such a process is disclosed in WO 94/00500.

The catalyst composition may be prepared as a homogeneous catalyst by addition of the requisite components to a solvent or diluent in which polymerization will be conducted. The catalyst composition may also be prepared and employed as a heterogeneous catalyst by adsorbing, depositing or chemically attaching the requisite components on an inorganic or organic particulated solid. Examples of such solids include, silica, silica gel, alumina, clays, expanded clays (aerogels), aluminosilicates, trialkylaluminum compounds, and organic or inorganic polymeric materials, especially polyolefins. In a preferred embodiment, a heterogeneous catalyst is prepared by reacting an inorganic compound, preferably a tri($C_{1-4}$ alkyl)aluminum compound, with an activating cocatalyst, especially an ammonium salt of a hydroxyaryl(trispentafluoro-phenyl)borate, such as an ammonium salt of (4-hydroxy-3,5-ditertiarybutylphenyl) tris-(pentafluorophenyl)borate or (4-hydroxyphenyl)-tris (pentafluorophenyl)borate. This activating cocatalyst is deposited onto the support by coprecipitating, imbibing, spraying, or similar technique, and thereafter removing any solvent or diluent. The metal complex is added to the support, also by adsorbing, depositing or chemically attaching the same to the support, either subsequently, simultaneously or prior to addition of the activating cocatalyst.

When prepared in heterogeneous or supported form, the catalyst composition is employed in a slurry or gas phase polymerization. As a practical limitation, slurry polymerization takes place in liquid diluents in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise, the α-olefin monomer or a mixture of different α-olefin monomers may be used in whole or part as the diluent. Most preferably, at least a major part of the diluent comprises the α-olefin monomer or monomers to be polymerized. A dispersant, particularly an elastomer, may be dissolved in the diluent utilizing techniques known in the art, if desired.

At all times, the individual ingredients as well as the recovered catalyst components must be protected from oxygen and moisture. Therefore, the catalyst components and catalysts must be prepared and recovered in an oxygen and moisture free atmosphere. Preferably, therefore, the reactions are performed in the presence of an dry, inert gas, such as, for example, nitrogen.

The polymerization may be carried out as a batchwise or a continuous polymerization process. A continuous process is preferred, in which event catalyst, ethylene, comonomer, and optionally solvent, are continuously supplied to the reaction zone, and polymer product continuously removed therefrom.

Without limiting in any way the scope of the invention, one means for carrying out such a polymerization process is as follows: In a stirred-tank reactor, the monomers to be polymerized are introduced continuously, together with solvent and an optional chain transfer agent. The reactor contains a liquid phase composed substantially of monomers, together with any solvent or additional diluent and dissolved polymer. If desired, a small amount of a "H"-branch inducing diene such as norbornadiene, 1,7-octadiene or 1,9-decadiene may also be added. Catalyst and cocatalyst are continuously introduced in the reactor liquid phase. The reactor temperature and pressure may be controlled by adjusting the solvent/monomer ratio, the catalyst addition rate, as well as by cooling or heating coils, jackets or both. The polymerization rate is controlled by the rate of catalyst addition. The ethylene content of the polymer product is determined by the ratio of ethylene to comonomer in the reactor, which is controlled by manipulating the respective feed rates of these components to the reactor. The polymer product molecular weight is controlled, optionally, by controlling other polymerization variables such as the temperature, monomer concentration, or by the previously mention chain transfer agent, such as a stream of hydrogen introduced to the reactor, as is well known in the art. The reactor effluent is contacted with a catalyst kill agent such as water. The polymer solution is optionally heated, and the polymer product is recovered by flashing off gaseous monomers as well as residual solvent or diluent at reduced pressure, and, if necessary, conducting further devolatilization in equipment such as a devolatilizing extruder. In a continuous process the mean residence time of the catalyst and polymer in the reactor generally is from about 5 minutes to 8 hours, and preferably from 10 minutes to 6 hours.

Ethylene homopolymers and ethylene/α-olefin copolymers are particularly suited for preparation according to the invention. Generally such polymers have densities from 0.85 to 0.96 g/ml. Typically the molar ratio of α-olefin comonomer to ethylene used in the polymerization may be varied in order to adjust the density of the resulting polymer. When producing materials with a density range of from 0.91 to 0.93 the comonomer to monomer ratio is less than 0.2, preferably less than 0.05, even more preferably less than 0.02, and may even be less than 0.01. In the above polymerization process hydrogen has been found to effectively control the molecular weight of the resulting polymer. Typically, the molar ratio of hydrogen to monomer is less than about 0.5, preferably less than 0.2, more preferably less than 0.05, even more preferably less than 0.02 and may even be less than 0.01.

Highly desirably the present catalyst compositions have been found to be highly effective in the preparation of the foregoing ethylene copolymers having an extremely low weight average molecular weight less than 100,000, preferably less than 50,000; a high comonomer incorporation greater than 5 weight percent, preferably greater than 10 weight percent (based on total polymer weight), and sufficient catalyst efficiency such that the polymerization can be conducted at solution polymerization temperatures from 95 to 160° C., preferably from 100 to 155° C., with catalyst efficiencies greater than 400,000 g polymer/g Ti, preferably greater than $1 \times 10^6$ g polymer/g Ti. Even more surprising, the foregoing copolymers are readily prepared using extremely low levels of hydrogen or other separately added chain transfer agent. In particular, the molar ratio of hydrogen to monomer is desirably less than 0.01.

More particularly, the resulting copolymers consisting essentially of ethylene and one or more $C_{4-10}$ α-olefins are low molecular weight polymers or waxes having a melt index, MI, greater than 10, preferably greater than 100, or even oils. The oils find particular use as viscosity modifying additives for lubricants. The resulting copolymers of ethylene, propylene, and optionally one or more of norbornadiene, ethylidene-norbornene, or a $C_{4-40}$ diene as well as the copolymers of ethylene, a $C_{4-10}$ α-olefin, and one or more of norbornadiene, ethylidene-norbornene, or a $C_{4-40}$ diene are low molecular elastomers or they are tackifiers or extenders for use in adhesive formulations, desirably having a Mooney viscosity from 0.01 to 10, preferably from 0.1 to 10.

EXAMPLES

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis. The term "overnight", if used, refers to a time of approximately 16–18 hours, "room temperature", if used, refers to a temperature of about 20–25° C., and "mixed alkanes" refers to a mixture of hydrogenated propylene oligomers, mostly $C_6$–$C_{12}$ isoalkanes, available commercially under the trademark Isopar E™ from ExxonMobil Chemicals Inc.

All syntheses and manipulations of air-sensitive materials were carried out in an inert atmosphere (nitrogen or argon) glove box. Solvents were first saturated with nitrogen and then dried by passage through activated alumina and Q-5™ catalyst prior to use. Deuterated NMR solvents were dried over sodium/potassium alloy and filtered prior to use. NMR spectra were recorded on a Varian INOVA 300 (FT 300 MHz, $^1$H; 75 MHz, $^{13}$C) spectrometer. Chemical shifts for $^1$H and $^{13}$C spectra were referenced to internal solvent resonances and are reported relative to tetramethylsilane. Mass spectra were recorded on a VG Autospec (S/N V190) mass spectrometer. Coupling constants are reported in hertz (Hz). The 3,4-diphenyl-3-cyclopenten-1-ol was prepared according to literature procedure—Corey, E. J.; Uda, H. *J. Am. Chem. Soc.* 1963, 85, 1788–1792.

Melt Index values are determined according to ASTM D-1238, 190° C./2.16 kg.

Mooney Viscosities are determined according to ASTM D1646-94, ML(1+4) at 125° C.

Example 1 dichloro[N-(1,1-dimethylethyl)-1,1-dimethyl-1-[(1,2,3,4,5-η)-3,4-diphenyl-2,4-cyclopentadien-1-yl]silanaminato(2-)-κN]-titanium

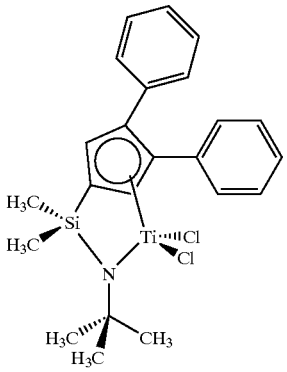

A) Preparation of 3,4-diphenyl-3-cyclopentene-1-sulfonyl chloride.

3,4-Diphenyl-3-cyclopenten-1-ol (5.91 g) was dissolved in the mixture of 70 mL of methylene chloride and 50 mL of pyrridine. To this reaction mixture was added 4 mL of $CH_3SO_3Cl$. After stirring overnight and reaction mixture was washed with 1 M of HCl, $H_2O$ and $NaHCO_3$. Solution was dried over $Mg_2SO_4$ and then filtered. Solvent removal gave brown solid. About 8 mL of ethyl acetate was added followed by 150 mL of hexane producing off-white crystalline solid). After stirring overnight solid was collected on the frit, washed with 10 mL of hexane and then dried under reduced pressure to give 4.0 g of product.

$^1H$ (CDCl$_3$) δ 3.07 (s, 3H), 3.21 (dd, 2H, $^2J_{H-H}$=16.5 Hz, $^3J_{H-H}$=2.4 Hz), 3.40 (dd, 2H, $^2J_{H-H}$=16.8 Hz, $^3J_{H-H}$=6.6 Hz), 5.50 (m, 1H), 7.22 (m, 10H).

$^{13}C$ (CDCl$_3$) δ 38.49, 45.64, 79.21, 127.23, 128.04, 128.20, 133.82, 136.45.

HRMS (EI): calculated for $C_{18}H_{18}O_3S$ 314.0977 found 314.0970.

B) Preparation of 1-(4-bromo-2-phenyl-1-cyclopenten-1-yl)benzene

To a mixture of 3,4-diphenyl-3-cyclopentene-1-sulfonyl chloride (4 g) and 3 g of LiBr was added 70 mnL of acetone. Reaction mixture was stirred under reflux for 2.5 hr. Solvent was removed under reduced pressure and the residue was extracted with 60 mL of methylene chloride. Solution was filtered and solvent was removed under reduced pressure giving 3.1 g of product as brown-yellow solid.

$^1H$ (CDCl$_3$) δ 3.35 (dd, 2H, $^2J_{H-H}$=16.2 Hz, $^3J_{H-H}$=3.6 Hz), 3.58 (dd, 2H, $^2J_{H-H}$=16.2 Hz, $^3J_{H-H}$=6.6 Hz), 4.78 (m, 1H), 7.23 (m, 10H).

$^{13}C$ (CDCl$_3$) δ 46.97, 50.21, 127.13, 128.05, 128.21, 135.15, 136.79.

HRMS (EI): calculated for $C_{17}H_{15}Br$ 298.0357 found 298.0338.

C) Preparation of (2,3-diphenyl-2,4-cyclopentadien-1-yl)potassium

To 2.93 g (9.79 mmol) of 1-(4-bromo-2-phenyl-1-cyclopenten-1-yl)benzene dissolved in 50 mL of toluene was added 4.10 g (20.6 mmol) of $KN(TMS)_2$ dissolved in 60 mL of toluene within 5 minutes. Within minutes yellow precipitate appeared. After stirring for 7 hours the solid was collected on the frit, washed with hexane and dried under reduced pressure to give 3.86 g of product.

$^1H$ (THF-d$^8$) δ 5.65 (t, 1H, $^3J_{H-H}$=3.3 Hz), 5.79 (d, 2H, $^3J_{H-H}$=3.3 Hz), 6.74 (t, 2H, $^3J_{H-H}$=7.5 Hz, para), 6.94 (t, 4H, $^3J_{H-H}$=7.5 Hz, meta), 7.18 (d, 4H, $^3J_{H-H}$=7.5 Hz, ortho).

$^{13}C$ (THF-d$^8$) δ 108.01, 110.24, 119.64, 121.97, 128.00, 128.25, 143.59.

HRMS (EI): calculated for $C_{17}H_{13}K$ 256.0654 found 256.0688.

D) Preparation of N-(tert-butyl)(3,4-diphenyl-2,4-cyclopentadien-1-yl)dimethylsilanamine

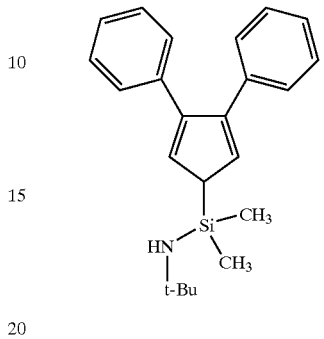

The solid (2,3-diphenyl-2,4-cyclopentadien-1-yl)potassium was partly dissolved in 50 mL of THF and was added to 12.64 g (97.93 mmol) of $Me_2SiCl_2$ dissolved in 40 mL of THF and 80 mL of ether. After stirring for 1 hr solvent was removed under reduced pressure and the residue was partly dissolved in 140 mL of toluene. To this solution was added 2.16 mL of $NH_2$-t-Bu and the reaction mixture was stirred overnight. The resulting solution was filtered and solvent was removed from the filtrate to leaving 2.67 g of orange thick oil.

HRMS (EI): calculated for $C_{23}H_{29}NSi$ 347.2069 found 347.2070

E) Preparation of dichloro [N-(1,1-dimethylethyl)-1,1-dimethyl-1-[(1,2,3,4,5-η)-3,4-diphenyl-2,4-cyclopentadien-1-yl]silanaminato(2-)-κN]-titanium.

The N-(tert-butyl)(3,4-diphenyl-2,4-cyclopentadien-1-yl)dimethylsilanamine (2.331 g, 6.71 mmol) and $Ti(NMe_2)_4$ 1.503 g, 6.71 mmol was dissolved in 50 mL of octane. Reaction mixture was refluxed overnight. The color changed from orange to deep red. Solvent was removed under reduced pressure to give thick red oil (3.229 g). Proton NMR showed formation of the desired bis(amido) complex in about 75 percent yield. To a 3.229 g of the red oil dissolved in 40 mL of toluene was added 8.6 g of $Me_2SiCl_2$. After stirring for 2 days solvent was removed under reduced pressure leaving dark solid. Hexane (50 mL) was added and the mixture was stirred for 3 hours. Green-yellow solid was collected on the frit, washed with cold hexane (20 mL) and dried under reduced pressure to give 1.66 g of product. Yield was 75 percent. The complex (0.71 g) was dissolved in 10 mL of toluene followed by 50 mL of hexane. After 2 minutes solution was filtered and put aside at room temperature. After a few minutes yellow crystals appeared. After 5 hours at room temperature additional crystals appeared and the solution was put into a −27° C. freezer overnight. Solvent was decanted and the crystals were washed with 15 mL of cold hexane to give 512 mg of product.

$^1H$ (C$_6$D$_6$) δ 0.32 (s, 6H, Si(CH$_3$)$_3$), 1.42 (s, 9H, C(CH$_3$)$_3$), 6.51 (s, 2H, H2), 702 (m, 6H), 7.54 (m, 4H).

$^{13}C\{^1H\}$ (C$_6$D$_6$) δ −0.10 (Si(CH$_3$)$_3$), 32.57 (C(CH$_3$)$_3$), 64.46 (C(CH$_3$)$_3$), 110.00 (C1), 126.27, 128.38, 128.72, 130.13, 133.98, 141.37.

HRMS (EI, (M-CH$_3$)$^+$): calculated for $C_{22}H_{22}NSiTiCl_2$ 448.0534 found 448.0534.

Elemental Analysis. Calculated for $C_{23}H_{25}NSiTiCl_2$: C, 59.49; H, 5.86; N, 3.02. Found: C, 59.25; H, 5.95; N, 3.42.

Example 2

[N-(1,1-dimethylethyl)-1,1-dimethyl-1-[(1,2,3,4,5-η)-3,4-diphenyl-2,4-cyclopentadien-1-yl] silanaminato(2-)-κN]-dimethyl-titanium

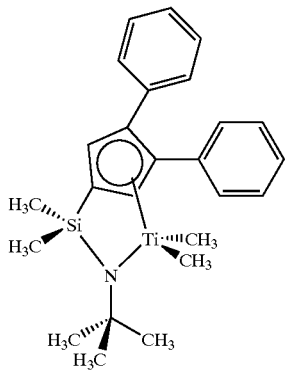

A) Preparation of [N-(1,1-dimethylethyl)-1,1-dimethyl-1-[(1,2,3,4,5-η)-3,4-diphenyl-2,4-cyclopentadien-1-yl]silanaminato(2-)-κN]-dimethyl-titanium.

In the drybox 0.41 g (0.89 mmol) of dichloro[N-(1,1-dimethylethyl)-1,1-dimethyl-1-[(1,2,3,4,5-η)-3,4-diphenyl-2,4-cyclopentadien-1-yl]silanaminato(2-)-κN]-titanium complex was dissolved in 30 ml of toluene. To this solution 1.2 mL (1.91 mmol) of MeLi (1.6 M in ether) was added dropwise while stirring over a 1 minute period. After the addition of MeLi was completed, the solution was stirred for 45 min. Toluene was removed under reduced pressure and the residue extracted with 35 mL of hot hexane. Solution was filtered hot and put into a −27 °C. freezer overnight. Solvent was decanted and the yellow crystals were washed with cold hexane and then dried under reduced pressure to give 272 mg of product. Yield was 74.5 percent.

$^1$H NMR (C$_6$D$_6$) δ 0.34 (s, 6H, Si(CH$_3$)$_3$), 0.78 (s, 6H, Ti(CH$_3$)$_3$), 1.56 (s, 9H, C(CH$_3$)$_3$), 6.18 (s, 2H, H2), 7.04 (m, 2H, para), 7.08 (m, 2H, meta), 7.49 (m, 4H, ortho).

$^{13}$C{$^1$H} (C$_6$D$_6$) δ 0.85 (Si(CH$_3$)$_3$), 34.54 (C(CH$_3$)$_3$), 56.27 (q, $^1J_{C-H}$=120.06 Hz, Ti(CH$_3$)$_3$), 59.68 (C(CH$_3$)$_3$), 104.88 (C1), 122.80 (C2), 127.56 (para), 128.49 (meta), 129.55 (ortho), 135.39, 135.90.

HRMS (EI, (M-CH$_3$)$^+$): calculated for C$_{24}$H$_{30}$NSiTi 408.1627 found 408.1624.

Elemental Analysis. Calculated for C$_{25}$H$_{33}$NSiTi: C, 70.90; H, 7.85; N, 3.31. Found: C, 70.64; H, 7.91; N, 3.06.

Polymerizations

Ethylene/1-Octene Polymerization Conditions I

All liquid and gas feeds were passed through columns of alumina and a decontaminant (Q-5™ catalyst available from Englehardt Chemicals Inc.) prior to introduction into the reactor. Catalyst components are handled in a glovebox containing an atmosphere of argon or nitrogen. A stirred 2.0 liter reactor is charged with 640 g of mixed alkanes solvent and 150 g of 1-octene comonomer. Hydrogen (20 psi, 170 kPa) is added by differential pressure expansion from a 75 mL addition tank. The reactor is heated to 100° C. and saturated with ethylene at 500 psig (3.4 MPa). Metal complex as dilute toluene solution and cocatalyst as dilute solutions in toluene or methycyclohexane were mixed in a 1:1 molar ratio and transferred to a catalyst addition tank and injected into the reactor. The cocatalyst was methyldi (octadecyl)ammonium tetrakis(pentafluoro-phenyl)borate (MDBP), the ammonium cation of which is derived from a mixture of amines available commercially as methyl bis (tallow)amine. The polymerization conditions were maintained for 15 minutes with ethylene added on demand. The resulting solution was removed from the reactor, quenched with isopropyl alcohol, and stabilized by addition of a toluene solution containing about 67 mg/100 g polymer of a hindered phenol antioxidant (Irganox™ 1010 from Ciba Geigy Corporation) and about 133 mg/100 g polymer of a phosphorus stabilizer (Irgafos™ 168 from Ciba Geigy Corporation).

Between sequential polymerization runs, a wash cycle was conducted in which 850 g of mixed alkanes was added to the reactor and the reactor was heated to 150° C. The reactor was then emptied of the heated solvent immediately before beginning a new polymerization run.

A polymer according to the invention and a comparison polymer were recovered by drying in a vacuum oven programmed to reach 140° C. over a period of about 20 hours. Density values are derived by determining the polymer's mass when in air and when immersed in methylethyl ketone. Results are contained in Table 1.

TABLE 1

Ethylene/Octene Polymerization Results

| Run | Catalyst μmoles | Yield (g) | Efficiency (g/μg Ti) | Density (g/mL) | Melt Index | Mw | MWD |
|---|---|---|---|---|---|---|---|
| 1* | ID$^1$ (0.05) | 48.4 | 22.6 | 0.877 | 0.06 | 246,047 | 2.06 |
| 2 | Ex. 2 (0.05) | 28.0 | 20.0 | 0.864 | >100 | 27,609 | 2.95 |

*comparative, not an example of the invention
$^1$(dimethyl(N-(tert-butyl)-1,1-dimethyl-1-((1,2,3,3a,8a-η)-1,5,6,7-tetrahydro-2-methyl-s-indacen-1-yl)-silanaminato(2-)-κN)-titanium) prepared as outlined in WO98/27103
2. melt index as determined by micromelt technique, equivalent to ASTM-D-1238, condition F.

Ethylene/1-Octene/Ethylidenenorbornene Polymerization Conditions

All liquid feeds except ethylidenenorbornene (ENB) and gas feeds were passed through columns of alumina and a decontaminant (Q-5™ catalyst available from Englehardt Chemicals Inc.) prior to introduction into the reactor. ENB was passed through a short column (3×10 cm) of alumina prior to introduction to the reactor. Catalyst components are handled in a glovebox containing an atmosphere of argon or nitrogen. A stirred 2.0 liter reactor is charged with about 640 g of mixed alkanes solvent, 150 g of 1-octene and 16 g of ENB. Hydrogen (20 psi, 140 kPa) is added by differential pressure expansion from a 75 mL addition tank. The reactor is heated to 100° C. and saturated with ethylene at 500 psig (3.5 MPa). Metal complex as dilute toluene solution and cocatalyst as dilute solutions in toluene were mixed in a 1:1 molar ratio and transferred to a catalyst addition tank and injected into the reactor. The cocatalyst was methyldi (octadecyl)ammonium tetrakis(pentafluorophenyl)borate (MDBP), the ammonium cation of which is derived from a mixture of amines available commercially as methyl bis (tallow)amine. The polymerization conditions were maintained for 15 minutes with ethylene added on demand. The resulting solution was removed from the reactor, quenched with isopropyl alcohol, and stabilized by addition of a toluene solution containing about 67 mg/100 g polymer of a hindered phenol antioxidant (Irganox™ 1010 from Ciba Geigy Corporation) and about 133 mg/100 g polymer of a phosphorus stabilizer (Irgafos™ 168 from Ciba Geigy Corporation).

Between sequential polymerization runs, a wash cycle was conducted in which 850 g of mixed alkanes was added to the reactor and the reactor was heated to 130° C. The reactor was then emptied of the heated solvent immediately before beginning a new polymerization run.

Polymers were recovered by drying in a vacuum oven set at 140° C. for about 20 hours. GPC results are determined by standard methods and are reported relative to a polystyrene/polyethylene universal calibration. The percent ethylene, 1-octene and ENB for the polymer and a comparison polymer were determined by IR spectroscopic analysis. Results are contained in Table 2.

TABLE 2

Ethylene/Octene/ENB Polymerization Results

| Run | Catalyst μmoles | Yield (g) | Efficiency (g/μg Ti) | Viscosity ML (1 + 4) | % ethylene | % octene | % ENB |
|---|---|---|---|---|---|---|---|
| 3* | ID[1] (0.95) | 92.5 | 2.03 | 125 | 75.4 | 20.3 | 4.4 |
| 4 | Ex. 2 (0.95) | 61.5 | 1.35 | <2 | 70.5 | 27.2 | 2.5 |

*comparative, not an example of the invention
[1](dimethyl(N-(tert-butyl)-1,1-dimethyl-1-((1,2,3,3a,8a-η)-1,5,6,7-tetrahydro-2-methyl-s-indacen-1-yl)-silanaminato(2-)-κN)-titanium) prepared as outlined in WO98/27103
2. melt index as determined by micromelt technique, equivalent to ASTM-D-1238, condition F.

Ethylene/Propylene/Ethylidenenorbornene Polymerization Conditions

All liquid feeds except ethylidenenorbornene (ENB) and gas feeds were passed through columns of alumina and a decontaminant (Q-5™ catalyst available from Englehardt Chemicals Inc.) prior to introduction into the reactor. ENB was passed through a short column (3×10 cm) of alumina prior to introduction to the reactor. Catalyst components are handled in a glovebox containing an atmosphere of argon or nitrogen. A stirred 2.0 liter reactor is charged with 780 g of mixed alkanes solvent, 16 g of ENB and hydrogen (20 psi, 140 kPa) is added by differential pressure expansion from a 75 mL addition tank. The reactor is then charged with 120 g of propylene and heated to 100° C. and saturated with ethylene at 450 psig. Metal complex as dilute toluene solution and cocatalyst as dilute solutions in toluene were mixed in a 1:1 molar ratio and transferred to a catalyst addition tank and injected into the reactor. The cocatalyst was methyldi(octadecyl)ammonium tetrakis(pentafluorophenyl)borate (MDBP), the ammonium cation of which is derived from a mixture of amines available commercially as methyl bis(tallow)amine. The polymerization conditions were maintained for 15 minutes with ethylene added on demand. The resulting solution was removed from the reactor, quenched with isopropyl alcohol, and stabilized by addition of a toluene solution containing about 67 mg/100 g polymer of a hindered phenol antioxidant (Irganox™ 1010 from Ciba Geigy Corporation) and about 133 mg/100 g polymer of a phosphorus stabilizer (Irgafos™ 168 from Ciba Geigy Corporation).

Between sequential polymerization runs, a wash cycle was conducted in which 850 g of mixed alkanes was added to the reactor and the reactor was heated to 130° C. The reactor was then emptied of the heated solvent immediately before beginning a new polymerization run.

Polymers were recovered by drying in a vacuum oven set at 140° C. for about 20 hours. GPC results are determined by standard methods and are reported relative to a polystyrene/polyethylene universal calibration. The percent ethylene, propylene and ENB for the polymer and a comparison polymer were determined by IR spectroscopic analysis. Results are contained in Table 3.

TABLE 3

Ethylene/Propylene/ENB Polymerization Results

| Run | Catalyst μmoles | Yield (g) | Efficiency (g/μg Ti) | Viscosity ML (1 + 4) | % ethylene | % propylene | % ENB |
|---|---|---|---|---|---|---|---|
| 5* | ID[1] (1.4) | 48.4 | 0.72 | 105 | 46.1 | 45.5 | 8.0 |
| 6 | Ex. 2 (1.4) | 28.0 | 0.42 | 5 | 47.4 | 47.3 | 5.6 |

*comparative, not an example of the invention
[1](dimethyl(N-(tert-butyl)-1,1-dimethyl-1-((1,2,3,3a,8a-η)-1,5,6,7-tetrahydro-2-methyl-s-indacen-1-yl)-silanaminato(2-)-κN)-titanium) prepared as outlined in WO98/27103
2. melt index as determined by micromelt technique, equivalent to ASTM-D-1238, condition F.

Continuous Solution Polymerization

A series of ethylene/(α-olefin interpolymers are prepared in a 4 liter, oil jacketed, continuously stirred tank reactor (CSTR). A magnetically coupled agitator provides mixing. The reactor is run liquid full at 475 psi (3,275 kPa). Process flow is in at the bottom and out of the top. A heat transfer oil is circulated through the jacket of the reactor to remove some of the heat of reaction. At the exit of the reactor is a flow meter that measured flow and solution density. All lines on the exit of the reactor are traced with 50 psi (300 kPa) steam and insulated.

Mixed alkanes solvent and comonomer are supplied to the reactor at 30 psi (200 kPa) pressure. The solvent feed to the reactors is measured by a mass flow meter. A variable speed diaphragm pump controls the solvent flow rate and increases the solvent pressure to reactor pressure. The comonomer is metered by a mass flow meter and flow controlled by a control valve. The comonomer stream is mixed with the solvent stream at the suction of the solvent pump and is pumped to the reactor with the solvent. The remaining solvent is combined with ethylene and (optionally) hydrogen and delivered to the reactor. The ethylene stream is measured by a mass flow meter just prior to the flow control valve. Three flow meter/controllers (one limited to maximum 200 scm³/min. and two limited to a maximum of 100 scm³/min. flow) are used to deliver hydrogen into the ethylene stream at the outlet of the ethylene control valve.

The ethylene or ethylene/hydrogen mixture is combined with the solvent/comonomer stream at ambient temperature. The temperature of the solvent/monomer stream entering the bottom of the reactor is controlled with two heat exchangers.

In an inert atmosphere box, a solution of the transition metal compound is prepared by mixing the appropriate volumes of concentrated solutions with additional solvent to provide the final catalyst solution of known concentration and composition. This solution is transferred under nitrogen to a pressure vessel attached to a high-pressure metering pump for transport to the polymerization reactor.

In the same inert atmosphere box, solutions of a cocatalyst mixture, MDBP and modified methylalumoxane (CAS 146905-79-10, MMAO Type 3A, available form Akzo Nobel) are prepared in mixed alkanes solvent and transferred to separate pressure vessels. The molar ratio of Al to Ti (6.00) and B to Ti (1.25) are established by controlling the volumetric flow output using metering pumps attached to each pressure vessel and connected to an inlet in the bottom of the reactor.

Polymerization is conducted at 150° C. and stopped with the addition of catalyst kill into the reactor product line after the meter measuring the solution density. The reactor effluent stream then enters a post reactor heater that provides additional energy for solvent removal. Solvent is flash removed as the effluent exits the post reactor heater and the pressure is released.

This flashed polymer next enters a hot oil jacketed devolatilizer where approximately 90 percent of the volatiles are removed from the polymer. The remaining polymer stream is condensed with a chilled water jacketed exchanger and then enters a glycol jacket solvent/ethylene separation vessel. Solvent is removed from the bottom of the vessel and ethylene is vented from the top. The quantity of vented ethylene is measured with a mass flow meter. The devolatilized polymer exits the devolatilizer through a gear pump. The product is collected in lined pans and dried in a vacuum oven at 140° C. for 24 hr.

The polymers are stabilized with approximately 1000 ppm Irganox 1010 and 2000 ppm Irgafos 168 stabilizers obtained from Ciba Geigy Corporation. Stabilizers are added in combination with the catalyst kill. Table 4 summarizes the polymerization results.

TABLE 4

Continuous Ethylene/1-Octene Copolymerization Results

| Run | Cat. | $C_8$ Flow (kg/hr) | $H_2$ Flow (scc/min) | $C_2H_4$ Conversion (percent) | Efficiency (g poly./μg Ti) | Viscosity (Pa·s) | Density (g/cm$^3$) |
|---|---|---|---|---|---|---|---|
| 7* | TC[1] | 0.612 | 108 | 90.0 | 1.12 | 3.199 | 0.9034 |
| 8 | Ex. 2 | 0.454 | 24 | 90.4 | 1.02 | 3.132 | 0.9047 |

*comparative, not an example of the invention
[1](N-(t-butyl)-1,1-dimethyl-1-(tetramethylcyclopentadienyl)silanaminato(2-)-κN)-titanium (II) 1,3-pentadiene By comparison of the results of Table 4 it may be seen that low molecular weight copolymers having essentially equivalent properties can be produced while employing much lower hydrogen levels according to the present invention.

E. Continuous Ethylene/Propylene/Ethylidene-norbornene Copolymerization

A series of ethylene/propylene/ethylidene-norbornene copolymers are prepared in a 6.8 L, oil jacketed, continuously stirred tank reactor (CSTR) under conditions substantially identical to those recited in preparation D, excepting the comparison catalyst is (dimethyl(N-(tert-butyl)-1,1-dimethyl-1-((1,2,3,3a,8a-η)-1,5,6,7-tetrahydro-2-methyl-s-indacen-1-yl)-silanaminato(2-)-κN)-titanium) (ID), prepared as outlined in WO98/27103, and the molar ratio of Ti:B:Al employed is 1:1.1:11. Comonomer content of the polymers are determined by Fourier Transform IR analysis. Results are summarized in Table 5.

TABLE 5

| Catalyst | ID* | Ex. 2 |
|---|---|---|
| Temp ° C. | 95 | 95 |
| $C_2H_4$ Conversion (percent) | 85 | 85 |
| Production Rate (kg/hr) | 0.49 | 0.49 |
| Ethylene (kg/hr) | 0.39 | 0.39 |
| Propylene (kg/hr) | 0.24 | 0.24 |
| ENB (kg/hr) | 0.026 | 0.026 |
| Efficiency (g polymer/μg Ti) | 0.98 | 0.21 |
| Hydrogen (scm$^3$/min) | 10.5 | 10.6 |
| Mooney Viscosity | 22 | <2 |
| Percent $C_2H_4$ | 69.2 | 68.7 |
| Percent $C_3H_6$ | 28.6 | 26.0 |
| Percent ENB | 2.2 | 5.3 |

*Comparative, not an example of the invention

What is claimed is:

1. A polymerization process comprising contacting one or more addition polymerizable monomers selected from the group consisting of ethylene and one or more $C_{4-10}$ α-olefins under polymerization conditions including a temperature from 95 to 160° C. with a catalyst composition comprising a metal complex corresponding to the formula:

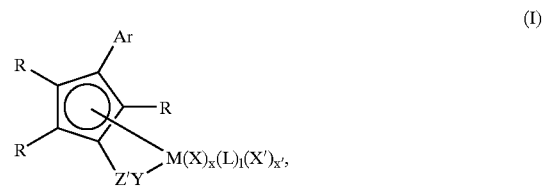

(I)

wherein,

Ar is an aryl group of from 6 to 30 atoms not counting hydrogen;

R independently each occurrence is hydrogen, Ar, or a group other than Ar selected from hydrocarbyl, trihydrocarbylsilyl, trihydrocarbylgermyl, halide, hydrocarbyloxy, trihydrocarbylsiloxy, bis(trihydrocarbylsilyl)amino, di(hydrocarbyl)amino, hydrocarbadiylamino, hydrocarbylimino, di(hydrocarbyl)phosphino, hydrocarbadiylphosphino, hydrocarbylsulfido, halo-substituted hydrocarbyl, hydrocarbyloxy-substituted hydrocarbyl, trihydrocarbylsilyl-substituted hydrocarbyl, trihydrocarbylsiloxy-substituted hydrocarbyl, bis(trihydrocarbylsilyl)amino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said R group having up to 40 atoms not counting hydrogen atoms;

M is titanium;

Z' is $SiR^6{}_2$, $CR^6{}_2$, $SiR^6{}_2SiR^6{}_2$, $CR^6{}_2CR^6{}_2$, $CR^6{=}CR^6$, $CR^6{}_2SiR^6{}_2$, $BR^6$, $BR^6L''$, or $GeR^6{}_2$;

Y is —O—, —S—, —NR$^5$—, —PR$^5$—; —NR$^5{}_2$, or —PR$^5{}_2$;

$R^5$, independently each occurrence, is hydrocarbyl, trihydrocarbylsilyl, or trihydrocarbylsilylhydrocarbyl, said $R^5$ having up to 20 atoms other than hydrogen, and optionally two $R^5$ groups or $R^5$ together with Y form a ring system;

$R^6$, independently each occurrence, is hydrogen, or a member selected from hydrocarbyl, hydrocarbyloxy, silyl, halogenated alkyl, halogenated aryl, —NR$^5{}_2$, and combinations thereof, said $R^6$ having up to 20 non-hydrogen atoms, and optionally, two $R^6$ groups form a ring system;

L'' is a monodentate or polydentate Lewis base optionally bonded to $R^6$;

X is hydrogen or a monovalent anionic ligand group having up to 60 atoms not counting hydrogen;

L independently each occurrence is a neutral ligating compound having up to 20 atoms, other than hydrogen, and optionally L and X are bonded together;

X' is a divalent anionic ligand group having up to 60 atoms other than hydrogen;

z is 0, 1 or 2;

x is 0, 1, 2, or 3;

l is a number from 0 to 2, and x' is 0 or 1, to prepare a polymer having a melt index greater than 1.0 and a comonomer incorporation greater than 5 weight percent.

2. A process according to claim 1, wherein at least one R is selected from the group consisting of Ar.

3. A process according to claim 2, wherein the cyclopentadienyl group is substituted at the 3- and 4-position with an Ar group.

4. A process according to any one of claims 1–3, wherein:

Ar is phenyl, naphthyl, 4-bisphenyl, 3-(N,N-dimethylamino)phenyl, 4-methoxyphenyl, 4methylphenyl, pyrrol-1-yl, or 1-methylpyrrol-3-yl;

R is hydrogen, methyl or Ar;

X is chloride, methyl or benzyl;

X' is 2,3-dimethyl-1,3-butenediyl;

L is 1,3-pentadiene or 1,4-diphenyl-1,3-butadiene;

Y is —$NR^5$—;

Z' is $SiR^6_2$;

$R^5$ each occurrence is independently hydrocarbyl;

$R^6$ each occurrence is independently methyl;

x is 0 or 2;

l is 0 or 1; and x' is 0 or 1;

with the proviso that:

when x is 2, x' is zero, and M is in the +4 formal oxidation state, when x is 0 and x' is 1, M is in the +4 formal oxidation state, and when x and x' are both 0, l is 1, and M is in the +2 formal oxidation state.

5. A process according to claim 1 wherein the metal complex is selected from the group consisting of:

(3,4-diphenylcyclopentadien-1-yl)dimethyl(t-butylamido)silanetitanium dichloride, (3,4-diphenylcyclopentadien-1-yl)dimethyl(t-butylamido)silanetitanium dimethyl, and (3,4-diphenylcyclopentadien-1-yl)dimethyl(t-butylamido)silanetitanium (II) 1,3-pentadiene.

6. A process according to any one of claims 1–3 which is a solution polymerization.

7. A process according to claim 4 which is a solution polymerization.

8. A polymerization process comprising contacting ethylene, propylene, and optionally one or more of norbornadiene, ethylidene-norbornene, or a $C_{4-40}$ diene or contacting ethylene, a $C_{4-10}$ α-olefin, and one or more of norbornadiene, ethylidene-norbornene, or a $C_{4-40}$ diene under polymerization conditions including a temperature from 95 to 160° C. with a catalyst composition comprising a metal complex corresponding to the formula:

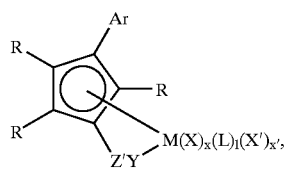

(I)

wherein,

Ar is an aryl group of from 6 to 30 atoms not counting hydrogen;

R independently each occurrence is hydrogen, Ar, or a group other than Ar selected from hydrocarbyl, trihydrocarbylsilyl, trihydrocarbylgermyl, halide, hydrocarbyloxy, trihydrocarbylsiloxy, bis(trihydrocarbylsilyl)amino, di(hydrocarbyl)amino, hydrocarbadiylamino, hydrocarbylimino, di(hydrocarbyl)phosphino, hydrocarbadiylphosphino, hydrocarbylsulfido, halo-substituted hydrocarbyl, hydrocarbyloxy-substituted hydrocarbyl, trihydrocarbylsilyl-substituted hydrocarbyl, trihydrocarbylsiloxy-substituted hydrocarbyl, bis(trihydrocarbylsilyl)amino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said R group having up to 40 atoms not counting hydrogen atoms;

M is titanium;

Z' is $SiR^6_2$, $CR^6_2$, $SiR^6_2SiR^6_2$, $CR^6_2CR^6_2$, $CR^6=CR^6$, $CR^6_2SiR^6_2$, $BR^6$, $BR^6L''$, or $GeR^6_2$;

Y is —O—, —S—, —$NR^5$—, —$PR^5$—; —$NR^5_2$, or —$PR^5_2$;

$R^5$, independently each occurrence, is hydrocarbyl, trihydrocarbylsilyl, or trihydrocarbylsilylhydrocarbyl, said $R^5$ having up to 20 atoms other than hydrogen, and optionally two $R^5$ groups or $R^5$ together with Y form a ring system;

$R^6$, independently each occurrence, is hydrogen, or a member selected from hydrocarbyl, hydrocarbyloxy, silyl, halogenated alkyl, halogenated aryl, —$NR^5_2$, and combinations thereof, said $R^6$ having up to 20 non-hydrogen atoms, and optionally, two $R^6$ groups form a ring system;

L'' is a monodentate or polydentate Lewis base optionally bonded to $R^6$;

X is hydrogen or a monovalent anionic ligand group having up to 60 atoms not counting hydrogen;

L independently each occurrence is a neutral ligating compound having up to 20 atoms, other than hydrogen, and optionally L and X are bonded together;

X' is a divalent anionic ligand group having up to 60 atoms other than hydrogen;

z is 0, 1 or 2;

x is 0, 1, 2, or 3;

l is a number from 0 to 2, and x' is 0 or 1, to prepare a polymer having a Mooney Viscosity from 0.01 to 10 and a comonomer incorporation greater than 5 weight percent.

9. A process according to claim 8, wherein at least one R is selected from the group consisting of Ar.

10. A process according to claim 8, wherein the cyclopentadienyl group is substituted at the 3- and 4-position with an Ar group.

11. A process according to any one of claims 8–10, wherein:

Ar is phenyl, naphthyl, 4-bisphenyl, 3-(N,N-dimethylamino)phenyl, 4-methoxyphenyl, 4-methylphenyl, pyrrol-1-yl, or 1-methylpyrrol-3-yl;

R is hydrogen, methyl or Ar;

X is chloride, methyl or benzyl;

X' is 2,3-dimethyl-1,3-butenediyl;

L is 1,3-pentadiene or 1,4-diphenyl-1,3-butadiene;
Y is —$NR^5$—;
Z' is $SiR^6{}_2$;
$R^5$ each occurrence is independently hydrocarbyl;
$R^6$ each occurrence is independently methyl;
x is 0 or 2;
l is 0 or 1; and
x' is 0 or 1;
with the proviso that:
when x is 2, x' is zero, and M is in the +4 formal oxidation state,
when x is 0 and x' is 1, M is in the +4 formal oxidation state, and
when x and x' are both 0, l is 1, and M is in the +2 formal oxidation state.

12. A process according to claim 8 wherein the metal complex is selected from the group consisting of:

(3,4-diphenylcyclopentadien-1-yl)dimethyl(t-butylamido)silanetitanium dichloride, (3,4-diphenylcyclopentadien-1-yl)dimethyl(t-butylamido)silanetitanium dimethyl, and (3,4-diphenylcyclopentadien-1-yl)dimethyl(t-butylamido)silanetitanium (II) 1,3-pentadiene.

13. A process according to any one of claims 8–10 which is a solution polymerization.

14. A process according to claim 12 which is a solution polymerization.

* * * * *